United States Patent [19]
Chabardes

[11] 3,978,135
[45] Aug. 31, 1976

[54] PREPARATION OF ETHERS FROM CITRONELLAL OR HOMOLOGUES THEREOF

[75] Inventor: Pierre Chabardes, Lyon, France

[73] Assignee: Rhone-Poulenc S.A., Paris, France

[22] Filed: Apr. 15, 1975

[21] Appl. No.: 568,323

Related U.S. Application Data

[63] Continuation of Ser. No. 317,082, Dec. 20, 1972, abandoned.

[30] Foreign Application Priority Data

Dec. 21, 1971  France .............................. 71.45873
Oct. 16, 1972  France .............................. 72.35673

[52] U.S. Cl. ........................... 260/602; 260/615 A; 252/522
[51] Int. Cl.² .................. C07C 47/20; C07C 45/02
[58] Field of Search ........... 260/602, 615 A; 317/82

[56] References Cited

UNITED STATES PATENTS

3,852,360  12/1974  Vilkas et al. ........................ 260/602

FOREIGN PATENTS OR APPLICATIONS

393,753  6/1933  United Kingdom ............. 260/615 A

Primary Examiner—James O. Thomas, Jr.
Assistant Examiner—W. B. Lone
Attorney, Agent, or Firm—Stevens, Davis, Miller & Mosher

[57] ABSTRACT

7-Alkoxydihydrocitronellals (and their homologues) and their acetals useful as perfumes are prepared from citronellal (or homologues thereof) by reaction with ammonia or a primary or secondary amine, followed by treatment of the product with an alkanol in the presence of a strong acid and then neutralization of the reaction mixture.

6 Claims, No Drawings

PREPARATION OF ETHERS FROM CITRONELLAL OR HOMOLOGUES THEREOF

This is a continuation of application Ser. No. 317,082, filed Dec. 20, 1972, now abandoned.

This invention relates to a process for the preparation of ethers of hydroxydihydrocitronellal (and homologues thereof) and to ether acetals.

The ethers of hydroxydihydrocitronellal itself correspond to the general formula:

$$RO-C(CH_3)_2-CH_2-CH_2-CH_2-CH(CH_3)-CH_2-CHO \quad (I)$$

in which R represents an alkyl radical.

Amongst the processes known for the preparation of these products, specially relevant is that described in French Patent Specification No. 1,173,539, from 2,6-dimethylocta-2,7-diene resulting from the pyrolysis of 1-pinane. This process consists firstly of adding an alcohol of the formula ROH to the diene in order to obtain a 2-alkoxy-2,6-dimethyloct-7-ene, which is epoxidised thereafter via an intermediate chlorohydrin. High temperature pyrolysis converts this alkoxyepoxide into 2-alkoxy-2,6-dimethyloctanal or the desired alkoxydihydrocitronellal. Another process described in French Patent Specification No. 1,403,943 uses 6-methyl-hept-5-en-2-one as the starting product, which, by reaction with an alcohol ROH, is converted into a 6-alkoxy-6-methyl-heptan-2-one, the ethinylation of which, by an alkali acetylide, leads to an ethinylcarbinol, which is then converted into an alkoxy-dimethyl-oct-2-enal or an alkoxy-citral by a succession of stages (i.e. esterification, catalytic rearrangement to the allene ester and hydrolysis), finally, a catalytic hydrogenation converts this alkoxycitral into an alkoxydihydrocitronellal. This process, which requires many stages, makes it possible to achieve yields of the order of 60%.

These processes are far from being as simple as those used to prepare hydroxydihydrocitronellal itself. The latter is prepared industrially from citronellal, a commercially available product extracted from vegetable oils, in very good yield: it is sufficient to hydrate citronellal after having blocked its aldehyde group in the form of the bisulphite derivative or the acetal in order to make hydration possible.

The present invention provides a process for the preparation of an alkyl ether of hydroxydihydrocitronellal or a homologue thereof which comprises the following steps a. reacting an aldehyde which is citronellal or a homologue thereof with a primary or secondary amine or ammonia b. contacting the product of step (a) with an alkanol in the presence of a strong acid and c. neutralizing the reaction mixture obtained in step b. with an alkaline reagent. It relates particularly to the preparation of ethers of hydroxydihydrocitronellal itself, which correspond to the general formula:

$$RO-C(CH_3)_2-CH_2-CH_2-CH_2-CH(CH_3)-CH_2-CHO \quad (I)$$

wherein R represents an alkyl radical. During this process, a certain amount of acetals of alkoxydihydrocitronellal can form as a result of acetalisation of the aldehyde group by the alcohol chosen for the etherification.

These acetals which, with their homologues, provide a further aspect of the invention, are of the formula:

$$RO-C(CH_3)_2-CH_2-CH_2-CH_2-CH(CH_3)-CH_2-CH(OR)_2 \quad (II)$$

wherein R represents an alkyl radical. They are new products with a pleasant smell and can be used in perfumery or in insecticidal compositions.

The process will be described with reference to citronellal as the aldehyde but it is equally applicable to homologues thereof.

The first step (a) of the process consists of reacting citronellal with ammonia or a primary or secondary amine; its purpose is to block the aldehyde group in order to protect it from secondary reactions which can take place during the addition of the chosen alcohol to citronellal, in the presence of a strong acid. An advantageous method of carrying out this first stage consists of allowing citronellal to react with an aliphatic, aromatic or cycloaliphatic, primary or secondary amine, preferably in an amount of at least one, especially one to two, mols of amine per mol of citronellal, an excess having no detrimental effect. If ammonia is used instead of an amine, it can be absorbed from the gaseous state by bubbling it through the citronellal or it can be added to the latter in the form of a preferably concentrated ammonia solution.

For this first stage, the temperature usually varies from −10°C. to +40°C., depending on the blocking agent chosen and is preferably −10°C. to +25°C. The water formed during the reaction can be removed by carrying out the reaction in the presence of a dehydrating agent such as an alkali metal carbonate; it can also be isolated at the end of the operation by decantation or by any other known method. Where the amine used is volatile, any excess can be removed therefrom by evaporation in vacuo before the second stage of the process is carried out. Amines such as methylamine, ethylamine, propylamines, butylamine, dimethylamine or diethylamine, are very suitable for this. In general, the amine is preferably aliphatic with for example 1 to 4 carbon atoms.

The second step (b) consists of adding an alcohol to the product resulting from the first step. What is involved is the addition of one molecule of this alcohol to the ethylenic bond of citronellal. This addition is carried out in the presence of a strong acid, such as hydrochloric acid or sulphuric acid, preferably in an amount of at least one mol per mol of citronellal used in step (a). About one mol of acid per mol of citronellal employed in step (a) is advantageous. The alcohol chosen is aliphatic, preferably with 1 to 6 carbon atoms e.g. methanol or ethanol; the molar quantity employed is preferably at least equivalent to that of the citronellal used. This reaction is preferably carried out at a low temperature e.g. at −20°C. to +50°C., especially −20°C. to +20°C. An advantageous means of controlling the reaction in order to avoid liberating the aldehyde group before or during the addition of the alcohol, consists of slowly pouring the product of the reaction between citronellal and ammonia or the amine into the chosen alcohol containing the acid; during this addition, the temperature of the reaction mixture is kept between −20°C and +50°C.

This strongly acidic reaction mixture is then neutralised in step (c) by means of an alkaline reagent such as an alkali metal hydroxide or an alkali metal carbonate preferably in the form of an aqueous solution. Where a volatile acid, such as hydrochloric acid, was chosen for the second stage, it is possible, prior to the neutralisation, to remove the majority of this acid by evaporation, and this process has the advantage of reducing the volume of the neutralisation mixture. During this neutralisation, hydrolysis takes place by which the aldehyde group of the desired alkoxydihydrocitronellal is liberated. To achieve this hydrolysis, a concentrated aqueous solution of the alkaline reagent is used, and this treatment with base is carried out in the cold or by heating to 40°–50°C. This neutralisation can be carried out in the presence of an organic solvent for the desired ether, and it is then more rapid and more effective and the formation of by-products is reduced.

During the process, a certain amount of acetals of hydroxydihydrocitronellal ethers can also form. This formation of acetals takes place to a greater or lesser extent depending on the working conditions, and the choice of conditions is a compromise which makes it possible to orient the reaction preferentially towards the preponderant formation of one or other of these products.

From the neutralisation mixture produced in step (c), the desired ether and/or acetal can be isolated by known methods. The products may be separated by any known means, usually by fractional distillation of the organic layer in vacuo. Products of a high degree of purity, which can be directly used in perfumery are thus obtained with good yields.

The following Examples illustrate the invention.

EXAMPLE 1

5.85 g ($1.3 \times 10^{-1}$ mol) of dimethylamine are introduced into a 100 cm$^3$ three-necked flask equipped with a stirrer, a dropping funnel, a condenser and a nitrogen flow system. 15.4 g ($1 \times 10^{-1}$ mol) of citronellal are run in, with stirring, over the course of 30 minutes, whilst keeping the temperature at between −5°C and 0°C.

The mixture is left to return to ambient temperature 20 cm$^3$ of diethyl ether are added and the water produced by the reaction is decanted. The ethereal solution is dried over potassium carbonate, the solution is filtered and the filtrate is concentrated without exceeding a temperature of 30°C in the mixture. The product thus obtained is a colourless limpid liquid.

34.3 g ($3.5 \times 10^{-1}$ mol) of sulphuric acid, dissolved in 55 cm$^3$ of methanol, are introduced into a 250 cm$^3$ three-necked flask equipped with a mechanical stirrer and a dropping funnel. The mixture is cooled to −10° and the product obtained above is run in over the course of 35 minutes whilst keeping the temperature at −10°C; the mixture is then left to return to ambient temperature and stirring is continued for 2 hours.

The reaction mixture is then diluted with 40 cm$^3$ of hexane and its pH is brought to 4 by means of a 30% aqueous sodium hydroxide solution, and then to 6 with a saturated aqueous sodium bicarbonate solution, without exceeding a temperature of 30°C. The sodium sulphate formed is filtered off and then taken up in water and its aqueous solution is extracted with 2 times 20 cm$^3$ of hexane. These hexane layers are combined with the organic layer, which originates from the decanting of the filtrate obtained during the isolation of the sodium sulphate. The combined hexane solution is washed with 25 cm$^3$ of a 5% aqueous solution of sulphuric acid and then with 25 cm$^3$ of a saturated aqueous sodium bicarbonate solution. The hexane solution is dried over potassium carbonate, filtered and the filtrate concentrated to yield a crude product in which 4.1 g of unreacted citronellal and 9.5 g of methoxydihydrocitronellal are found to be present by gas phase chromatography and nuclear magnetic resonance. The yield of methoxydihydrocitronellal is 69.5% and the proportion of citronellal converted is 73.5%

EXAMPLE 2

The first stage of the preceding example is repeated. The product obtained is then run into 49 cm$^3$ ($5 \times 10^{-1}$ mol) of sulphuric acid, dissolved in 85 cm$^3$ of methanol. When this reaction mixture is then treated under the conditions of the preceding example, it leads to a crude product in which 0.9 g of unreacted citronellal, 12.8 g of methoxydihydrocitronellal and 4.2 g of methyl acetal of methoxydihydrocitronellal are found to be present by the same means as before. The yield of methoxydihydrocitronellal is 73%, and 93% if its acetal is taken into account; the proportion of citronellal converted is 94%.

The methyl acetal of methoxydihydrocitronellal is a liquid product with a boiling point, b.p.$_{0.2\ mm}$ = 76°C and $n_D^{20}$ = 1.4325.

EXAMPLE 3

58.5 g (1.3 mols) of dimethylamine are introduced into a 500 cm$^3$ three-necked flask equipped with a dropping funnel, a reflux condenser and a nitrogen flow system. 154 g (1 mol) of citronellal are run in, with stirring, over the course of 35 minutes, whilst keeping the temperature at between 0°C and −2°C. The dropping funnel is washed with 25 cm$^3$ of diethyl ether. The mixture is left to return to ambient temperature and the water produced in the reaction is decanted. The ethereal solution is dried over potassium carbonate. The solution is filtered and the filtrate is concentrated without exceeding a temperature of 30°C in the mixture to obtain 240 cm$^3$ of product.

490 g (5 mols) of sulphuric acid, dissolved in 850 cm$^3$ of anhydrous methanol, are introduced into a 2 l three-necked flask equipped with a mechanical stirrer and a dropping funnel. The mixture is cooled to −10° and the product obtained above is run in, over the course of 30 minutes, whilst keeping the temperature at −10°C. The mixture is allowed to return to ambient temperature over the course of 1 hour and is left for 2 hours 15 minutes, whilst being stirred.

The reaction mixture is then treated as in the preceding Examples, dilution being carried out with 600 cm$^3$ of hexane, before neutralisation by means of sodium hydroxide followed by sodium bicarbonate until the pH is 6.

The combined hexane layers are treated in the same way as in the previous Examples to obtain a crude product which is rapidly distilled in a vacuum of 0.2 mm Hg at a temperature of 70°–85°C.

In the distillate, 14.4 g of unconverted citronellal, 89.5 g of methoxydihydrocitronellal and 30.4 g of the methyl acetal of methoxydihydrocitronellal are identified and their amount measured by nuclear magnetic resonance and gas phase chromatography. The yield of methoxydihydrocitronellal is 53.3%, and 67.8% when the acetal is taken into account. The degree of conversion is 90.5%.

EXAMPLE 4

15.4 g of citronellal are introduced into a 100 cm³ three-necked flask equipped with a stirrer, a dropping funnel, a condenser and a nitrogen flow system, and 7.4 g of butylamine are run in, over the course of 10 minutes, whilst restricting the temperature of the reaction mixture to 25°C at the most. The mixture is left to react for 5 minutes and is diluted with 20 cm³ of diethyl ether; the aqueous layer is decanted; the organic layer is dried over sodium sulphate, filtered and the filtrate concentrated.

34.3 g of sulphuric acid dissolved in 60 cm³ of methanol are introduced into a 250 cm³ three-necked flask equipped with a mechanical stirrer and a dripping funnel. The mixture is cooled to +10°C and the product obtained above is run in over the course of 15 minutes; the temperature is then allowed to return to +20°C and the mixture is stirred for 2 hours.

The reaction mixture is diluted with 30 cm³ of hexane and run into 67 g of a 30% aqueous sodium hydroxide solution, whilst keeping the temperature at 20°–25°C. Water is then added to dissolve the sodium sulphate formed, the organic layer is decanted and the aqueous layer is extracted 3 times with 50 cm³ of hexane. The combined hexane layers are washed with 3 times 30 cm³ of a 5% aqueous solution of sulphuric acid, then with 50 cm³ of a saturated aqueous sodium bicarbonate solution and then with 50 cm³ of water. The hexane solutions are dried over sodium sulphate, filtered and the filtrate concentrated to obtain a product in which 6.4 g of unconverted citronellal and 7.9 g of methoxydihydrocitronellal are shown to be present by gas phase chromatography and NMR. Yield 73%; proportion of citronellal converted 58%.

EXAMPLE 5

1.7 g of ammonia gas are absorbed slowly (duration of absorption 1 hour 20 minutes) in an apparatus identical to that of the preceding Example, which contains 15.4 g of citronellal and the temperature of which is kept at +25°C. The mixture is diluted with 20 cm³ of diethyl ether, the water is decanted, the organic layer is dried over sodium sulphate and filtered and the filtrate is concentrated by evaporating the diethyl ether. 16 cm³, weighing 15.45 g, of a colourless limpid liquid are thus isolated.

A solution of 17.15 g of concentrated sulphuric acid in 30 cm³ of methanol cooled to −10°C is prepared, into which 8 cm³ of the liquid obtained above are run over 15 minutes. The temperature is allowed to return to +20°C and the mixture is left to react for 2 hours. The reaction mixture is then diluted with 30 cm³ of hexane, and its pH is adjusted to 4 by adding a 20% aqueous sodium hydroxide solution, and then to 6 with an aqueous saturated sodium bicarbonate solution. The sodium sulphate formed is dissolved by adding water, the organic layer is decanted and the aqueous layer is extracted with 3 times 50 cm³ of hexane. The combined hexane layers are washed with 3 times 25 cm³ of a 5% aqueous solution of hydrochloric acid, and then with 25 cm³ of an aqueous saturated sodium bicarbonate solution.

By the same treatment as in the preceding Example, a product is isolated, in which 4.1 g of methoxydihydrocitronellal are found to be present in the same manner, corresponding to a yield of 44.5%.

EXAMPLE 6

58.5 g of dimethylamine are introduced into a 500 cm³ flask which contains 60 g of anhydrous potassium carbonate, cooled to −5°C, and then 154 g of citronellal are run in over the course of 45 minutes, the temperature of the flask being kept at between −5° and 0°C. The temperature of the flask is then allowed to return to +20°C and stirring is continued for 2 hours 30 minutes. After filtration, rinsing with 2 times 30 cm³ of hexane and concentration in vacuo, 196 g of an organic fraction are isolated and are run slowly (45 minutes) into a solution of 343 g of concentrated sulphuric acid and 550 cm³ of methanol. The reaction mixture, which was kept at +20°C during the addition, is then left to stand for 4 hours at ambient temperature, whilst being stirred. The mixture obtained is then poured into 667 g of a 30% aqueous sodium hydroxide solution. The sodium sulphate formed is dissolved by adding 1,500 cm³ of distilled water. The organic layer is then separated and the aqueous layer is extracted with 5 times 100 cm³ of hexane. The combined organic layers are washed with 3 times 500 cm³ of water. 200 cm³ of a 2.5% aqueous solution of sulphuric acid, followed by 160 cm³ of a saturated aqueous sodium bicarbonate solution are then added. The organic layer is isolated, dried over potassium carbonate, filtered and the filtrate concentrated. A fraction is thus obtained in which 8.5 g of unreacted citronellal and 153 g of methoxydihydrocitronellal are found to be present. Yield of methoxydihydrocitronellal: 87%. Proportion of citronellal converted: 94.5%.

I claim:

1. A process for the preparation of a $C_1$–$C_6$ alkyl ether of hydroxydihydrocitronellal which comprises the following steps:
    a. reacting citronellal with an aliphatic primary or secondary amine of 1 to 4 carbon atoms or ammonia at a temperature between −10°C and 40°C;
    b. contacting the product of step (a) with an alkanol of 1 to 6 carbon atoms, containing at least one mole of a strong inorganic acid per mole of citronellal employed in step (a) at a temperature between −20°c. and +50°C.; and
    c. neutralizing the reaction mixture obtained in step (b) with an alkaline reagent selected from the group consisting of alkali metal hydroxides and alkali metal carbonates.

2. A process according to claim 1 wherein at least an equimolar amount of the amine or ammonia is used in step (a).

3. A process according to claim 1 wherein step (a) is carried out at a temperature of −10°C. to +25°C.

4. A process according to claim 1 wherein in step (c) the alkaline reagent is present in aqueous solution.

5. A process according to claim 1 wherein in step (b) the strong acid is sulphuric acid.

6. A process according to claim 1 which comprises the following steps (a) reacting citronellal with about 1–3 mols of dimethylamine, butylamine or ammonia per mol of citronellal at −5°C. to −25°C. (b) contacting the product of step (a) with methanol at −10°C. to +20°C. in the presence of 3.5–5 mols sulphuric acid per mol of citronellal used in step (a) and (c) neutralising the reaction mixture of step (b) with an aqueous solution of sodium hydroxide to produce methoxydihydrocitronellal.

* * * * *